(12) United States Patent
Kim et al.

(10) Patent No.: US 10,576,010 B2
(45) Date of Patent: Mar. 3, 2020

(54) WALKING ASSISTANCE APPARATUS AND OPERATING METHOD THEREOF

(71) Applicant: Samsung Electronics Co., Ltd., Suwon-si, Gyeonggi-do (KR)

(72) Inventors: Kyung-Rock Kim, Yongin-si (KR); Keehong Seo, Seoul (KR); Jusuk Lee, Hwaseong-si (KR); Jun-Won Jang, Seoul (KR); Byung-Kwon Choi, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 201 days.

(21) Appl. No.: 15/643,683

(22) Filed: Jul. 7, 2017

(65) Prior Publication Data

US 2018/0177671 A1      Jun. 28, 2018

(30) Foreign Application Priority Data

Dec. 28, 2016   (KR) ................... 10-2016-0181273

(51) Int. Cl.
*A61H 3/00*   (2006.01)
*A61B 5/11*   (2006.01)
*A61B 5/00*   (2006.01)
*A61H 1/02*   (2006.01)
*A61H 1/00*   (2006.01)

(52) U.S. Cl.
CPC ............... *A61H 3/00* (2013.01); *A61B 5/112* (2013.01); *A61B 5/1123* (2013.01); *A61B 5/6812* (2013.01); *A61H 1/001* (2013.01); *A61H 1/0237* (2013.01); *A61H 2003/007* (2013.01); *A61H 2201/0192* (2013.01); *A61H 2201/1223* (2013.01); *A61H 2201/165* (2013.01); *A61H 2201/1645* (2013.01); *A61H 2201/5007* (2013.01); *A61H 2230/00* (2013.01)

(58) Field of Classification Search
CPC ...................................... A61B 5/11
See application file for complete search history.

(56) References Cited

U.S. PATENT DOCUMENTS 7,880,552 B2   2/2011   Yasuhara et al.
7,998,040 B2   8/2011   Kram et al.
(Continued)

FOREIGN PATENT DOCUMENTS

JP    2011-036367 A    2/2011
KR    10-0767192 B1   10/2007
(Continued)

OTHER PUBLICATIONS

Collins, Steven H. "Reducing the Energy Cost of Human Walking Using an Unpowered Exoskeleton", Nature (2015).
(Continued)

*Primary Examiner* — Yashita Sharma
(74) *Attorney, Agent, or Firm* — Harness, Dickey & Pierce, P.L.C.

(57) ABSTRACT

A walking assistance apparatus including a first fixing device and a second fixing device to be attached to both legs of a user, respectively, a motor device configured to provide an active assistance force to the first fixing device and the second fixing device using at least one motor, and a passive assistance force transmitter connected to the first fixing device and the second fixing device to provide a passive assistance force to the first fixing device and the second fixing device may be provided.

9 Claims, 9 Drawing Sheets

(56) References Cited

U.S. PATENT DOCUMENTS

| | | |
|---|---|---|
| 2009/0312682 A1 | 12/2009 | Hirata et al. |
| 2014/0163435 A1 | 6/2014 | Yamamoto et al. |
| 2014/0296761 A1 | 10/2014 | Yamamoto et al. |
| 2015/0231018 A1 | 8/2015 | Shim et al. |
| 2015/0272811 A1 | 10/2015 | Choi et al. |
| 2015/0321342 A1 | 11/2015 | Smith et al. |
| 2017/0049658 A1 | 2/2017 | Kim et al. |

FOREIGN PATENT DOCUMENTS

| | | |
|---|---|---|
| KR | 10-1390219 B1 | 4/2014 |
| KR | 10-1641344 B1 | 7/2016 |

OTHER PUBLICATIONS

Tsukahara, Atsushi "Sit-to-Stand and Stand-to-Sit Transfer Support for Complete Paraplegic Patients With Robot Suit HAL", Advanced Robotics 24 (2010) pp. 1615-1638.

WALKING ASSISTANCE APPARATUS AND OPERATING METHOD THEREOF

CROSS-REFERENCE TO RELATED APPLICATION

This application claims priority under 35 U.S.C. § 119 to Korean Patent Application No. 10-2016-0181273, filed on Dec. 28, 2016, in the Korean Intellectual Property Office, the entire contents of which are incorporated herein by reference in their entirety.

BACKGROUND

1. Field

At least some example embodiments relate to walking assistance apparatuses and/or operating methods thereof, and more particularly, to walking assistance apparatuses and/or operating methods thereof that may provide an assistance force using an elastic body, which is connected between both legs of a user to provide a passive assistance force thereto.

2. Description of the Related Art

A wearable walking assistance apparatus to be worn on an exoskeleton of a body improves walking by providing an assistance force with respect to a muscular strength during walking. For example, a walking assistance apparatus that provides an assistance torque to both hip joint portions of a user using a motor is used.

A general walking assistance apparatus provides an assistance force using a motor both in a positive work period, in which a force is applied in a direction the same as a direction in which a leg moves, and in a negative work period, in which a force is applied in a direction opposite to the direction in which the leg moves in a gait cycle. Thus, the walking assistance apparatus is optimized in terms of energy efficiency.

In a human walking mechanism, a kinetic energy is stored and used using an elastic body part (e.g., a ligament or muscle). By applying a walking mechanism using elasticity to an assistance force provided by the walking assistance apparatus, energy efficiency of the walking assistance apparatus may be improved.

SUMMARY

Some example embodiments relate to walking assistance apparatuses.

In some example embodiment, the walking assistance apparatus may include a first fixing device and a second fixing device to be attached to both legs of a user, respectively, a motor device configured to provide an active assistance force to the first fixing device and the second fixing device using at least one motor, and a passive assistance force transmitter connected to the first fixing device and the second fixing device to provide a passive assistance force to the first fixing device and the second fixing device.

The passive assistance force transmitter may include at least one elastic element, and the passive assistance force transmitter may be configured to store an elastic energy while the user is in a negative work period in a gait cycle, and provide the passive assistance force using the elastic energy. The apparatus may further include a passive assistance force controller configured to control a magnitude of the passive assistance force provided by the passive assistance force transmitter.

The passive assistance force controller may be configured to control the magnitude of the passive assistance force by controlling a length of the passive assistance force transmitter. The passive assistance force controller may be configured to control the magnitude of the passive assistance force using at least one motor connected to at least one end portion of the passive assistance force transmitter.

The apparatus may further include a motor device controller configured to control the motor device to adjust a magnitude of the active assistance force provided to the first fixing device and the second fixing device. The motor device controller may be configured to determine the magnitude of the active assistance force based on a magnitude of the passive assistance force.

The motor device controller may be configured to determine a total assistance force to be provided to each of the first fixing device and the second fixing device, and calculate the magnitude of the active assistance force by subtracting a contribution portion corresponding to the passive assistance force from the total assistance force.

The first fixing device and the second fixing device may include a first support and a second support configured to support portions of circumferences of the legs of the user, respectively, and the passive assistance force transmitter may be configured to connect the first support and the second support.

The first fixing device may be attached to a right thigh of the user, and the second fixing device may be attached to a left thigh of the user. The passive assistance force transmitter may be configured to enclose both the legs of the user.

Some example embodiments relate to computer-implemented operating methods of a walking assistance apparatus.

In some example embodiments, the method may include identifying a gait cycle of a user, calculating a total assistance force to be provided to each of both legs of the user, calculating a passive assistance force to be provided by a passive assistance force transmitter connected to a first fixing device and a second fixing device that are attached to both the legs of the user, respectively, determining an active assistance force to be provided to each of both the legs of the user based on the total assistance force and the passive assistance force, and providing the active assistance force to the first fixing device and the second fixing device using at least one motor.

The passive assistance force transmitter may include at least one elastic element, and the calculating a passive assistance force comprises storing an elastic energy while the user is in a negative work period in the gait cycle, and providing the passive assistance force using the elastic energy.

The method may further include adjusting a magnitude of the passive assistance force by controlling a length of the passive assistance force transmitter.

The determining an active assistance force may include calculating a magnitude of the active assistance force by subtracting a contribution portion corresponding to the passive assistance force from the total assistance force.

The first fixing device and the second fixing device may include a first support and a second support configured to support portions of circumferences of the legs of the user, respectively, and the passive assistance force transmitter may be configured to connect the first support and the second support.

The first fixing device may be attached to a right thigh of the user, and the second fixing device may be attached to a left thigh of the user.

At least one example embodiment relate to a non-transitory computer-readable recording medium storing computer readable instructions, which when executed by a computer, configure the computer to perform the aforementioned methods.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
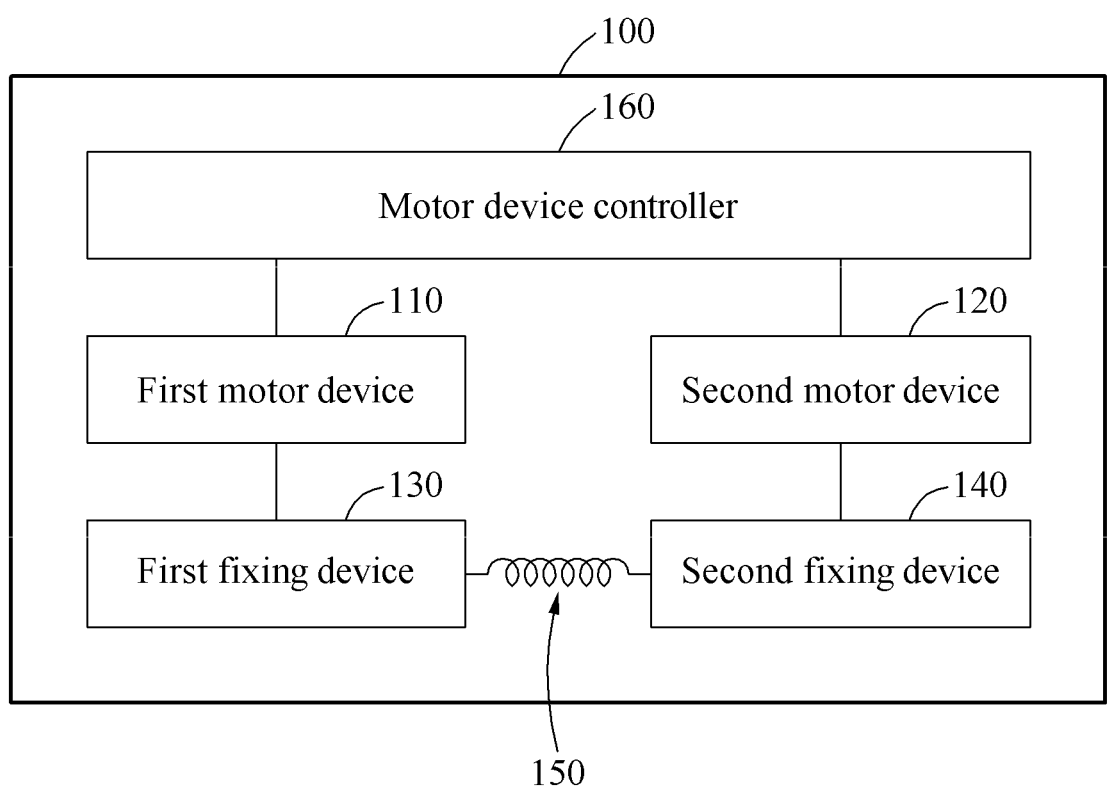
FIG. 1 is a block diagram illustrating a configuration of a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of the example embodiments, detailed description of well-known related structures or functions will be omitted when it is deemed that such description will cause ambiguous interpretation of the present disclosure.

It should be understood, however, that there is no intent to limit example embodiments to the particular example embodiments disclosed herein. On the contrary, the example embodiments are to cover all modifications, equivalents, and alternatives falling within the scope of example embodiments of the present inventive concepts. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is a block diagram illustrating a configuration of a walking assistance apparatus according to at least one example embodiment. Referring to FIG. 1, a walking assistance apparatus 100 may include a first motor device 110, a second motor device 120, a first fixing device 130, a second fixing device 140, a passive assistance force transmitter 150, and a motor device controller 160.

Hereinafter, the walking assistance apparatus 100 will be described based on an operation of a hip-type walking assistance apparatus. However, example embodiments are not limited thereto. The description may also be applied to another type of walking assistance apparatus without departing from the spirit and scope of example embodiments.

The walking assistance apparatus 100 may identify a gait cycle of a user based on a sensed gait motion of the user, and provide an assistance force of a variable magnitude to a hip joint portion of the user based on the gait motion of the user. The assistance force provided by the walking assistance apparatus 100 to the user may be, for example, an assistance torque provided to the hip joint portion of the user.

For example, the first motor device 110 and the second motor device 120 may be mechanically connected to both legs of the user, respectively, to provide an assistance torque in a direction to push or pull a swinging leg. An assistance force provided using a motor may be referred to as an active assistance force because the force is provided actively through a control of the motor.

The first fixing device 130 and the second fixing device 140 may be, for example, a set of frames attached to both legs of the user, respectively, to support the legs of the user and transmit the assistance force to the user. The first fixing device 130 and the second fixing device 140 each may include a tightener to be in close contact with a circumference of a leg of the user. According to some example embodiments, the first fixing device 130 and the second fixing device 140 each may include only a support configured to support a portion of the circumference of the leg of the user, instead of the tightener to be in close contact with the circumference of the leg of the user. Further, the first fixing device 130 and the second fixing device 140 each may include an assistance force transmitter (not shown) configured to transmit the assistance force provided by the first motor device 110 and the second motor device 120 to the user.

The passive assistance force transmitter 150 may be physically connected between the first fixing device 130 and the second fixing device 140. When a distance between (i) a position at which the passive assistance force transmitter 150 is connected to the first fixing device 130 and (ii) a position at which the passive assistance force transmitter 150 is connected to the second fixing device 140 is greater than or equal to a desired (or, alternatively predetermined) distance, the passive assistance force transmitter 150 may provide an assistance force in a direction to pull the first fixing device 130 and the second fixing device 140 toward each other. The assistance force provided using the passive assistance force transmitter 150 may be referred to as a passive assistance force because the force is provided passively in response to movements of the first fixing device 130 and the second fixing device 140.

A magnitude of the passive assistance force provided by the passive assistance force transmitter 150 may be controlled to a desired magnitude by a passive assistance force controller (not shown). The passive assistance force controller may include a passive assistance force calculator and at least one motor. The passive assistance force calculator may calculate the magnitude of the passive assistance force to be provided by the passive assistance force transmitter 150. To apply the calculated passive assistance force, the at least one motor may change a property such as a length or an elasticity of the passive assistance force transmitter 150. For example, the at least one motor may be connected to at least one end portion of the passive assistance force transmitter 150 to control the magnitude of the passive assistance force of the passive assistance force transmitter 150 based on the calculated passive assistance force. The passive assistance force transmitter 150 may include a desired (or, alternatively predetermined) elastic element such as a rubber band and/or a spring. When the passive assistance force transmitter 150 is an elastic element, a passive assistance force to be provided may depend on a spring constant of the elastic element. A length and the spring constant of the elastic element may be determined to have desired (or, alternatively predetermined) initial values through experiments and optimization, and may be customized or adjusted based on user information.

The passive assistance force transmitter 150 may be used efficiently in a negative work period in which a force is applied in a direction opposite to a direction in which a leg moves. The negative work period in a gait cycle of the user may appear in a period in which a swinging leg gradually reduces a swinging speed and stops, and a period in which a standing leg switches to swing. Because the passive assistance force transmitter 150 provides the assistance force when the distance between (i) the position at which the passive assistance force transmitter 150 is connected to the first fixing device 130 and (ii) the position at which the passive assistance force transmitter 150 is connected to the second fixing device 140 is greater than or equal to the desired (or, alternatively predetermined) distance, the passive assistance force transmitter 150 may provide a passive assistance force suitable for the negative work period through experiments and optimization.

The motor device controller 160 may control each of the at least one motor included in the first motor device 110 and the second motor device 120 to adjust a magnitude of the active assistance force to be transmitted by the first motor device 110 and the second motor device 120 to both the legs of the user through the first fixing device 130 and the second fixing device 140.

The motor device controller 160 may calculate a total assistance force to be provided to each of both the legs of the user, calculate a passive assistance force to be provided by the passive assistance force transmitter 150 based on a gait motion of the user in a current gait cycle, and calculate a magnitude of an active assistance force by subtracting a contribution portion corresponding to the passive assistance force from the total assistance force.

The total assistance force and the active assistance force may be torques to be applied to a hip joint, and the passive assistance force may be an elastic force to be applied between the fixing devices. In this example, the contribution portion corresponding to the passive assistance force may be a value obtained by converting the elastic force to a torque to be applied to the hip joint.

The total assistance force to be applied to each of both the legs of the user may vary based on a gait motion of the user, and the passive assistance force transmitter 150 may provide a variable passive assistance force based on the gait motion of the user. Thus, the motor device controller 160 may control the first motor device 110 and the second motor device 120 to provide a variable active assistance force.

As described above, the walking assistance apparatus 100 may provide a passive assistance force in a portion of periods using the passive assistance force transmitter 150, thereby reducing energy consumption for using a motor device in the corresponding portion of periods.

Figure 2:
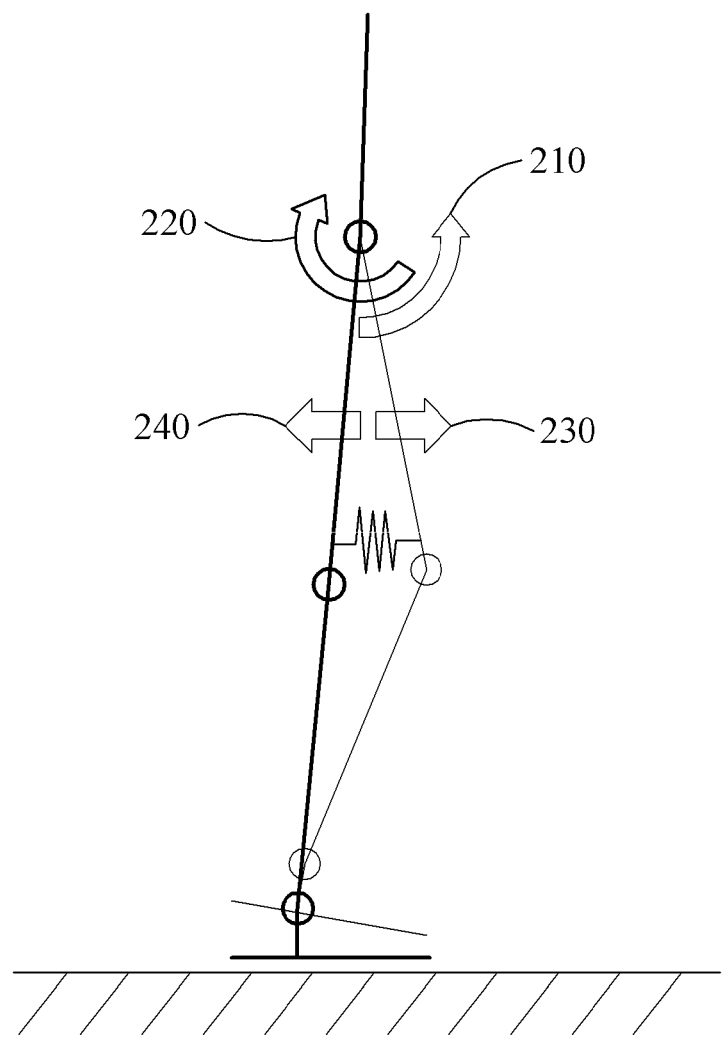
FIG. 2 illustrates an operating principle of a walking assistance apparatus according to at least one example embodiment.
Figure 3:
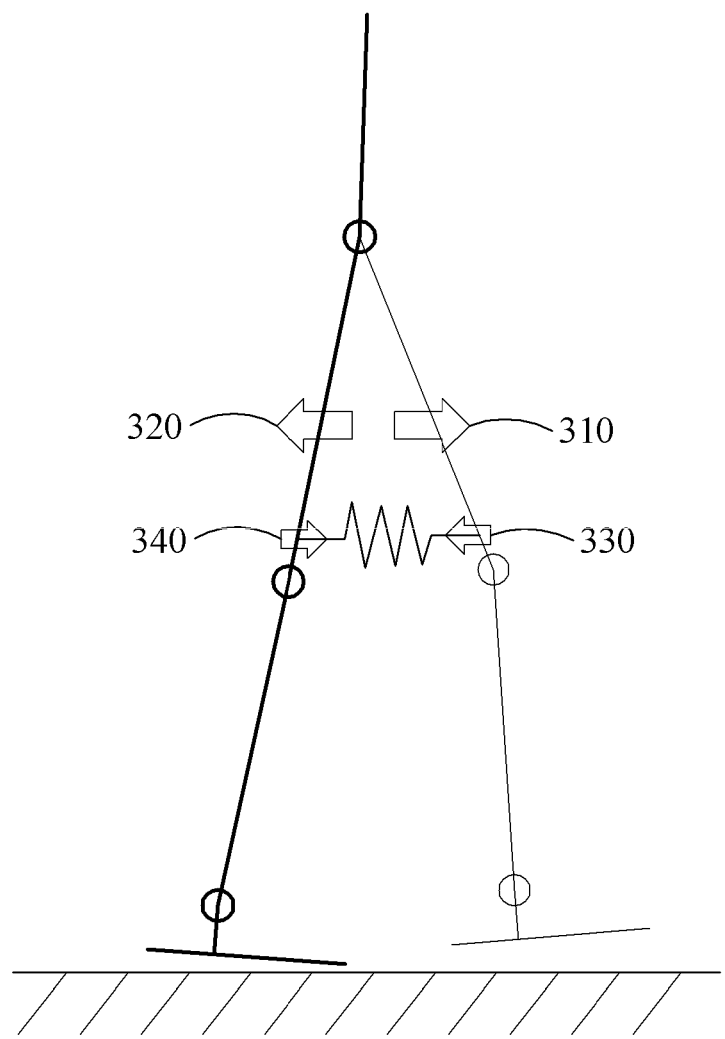
FIG. 3 illustrates an operating principle of a walking assistance apparatus according to at least one example embodiment.
Figure 4:
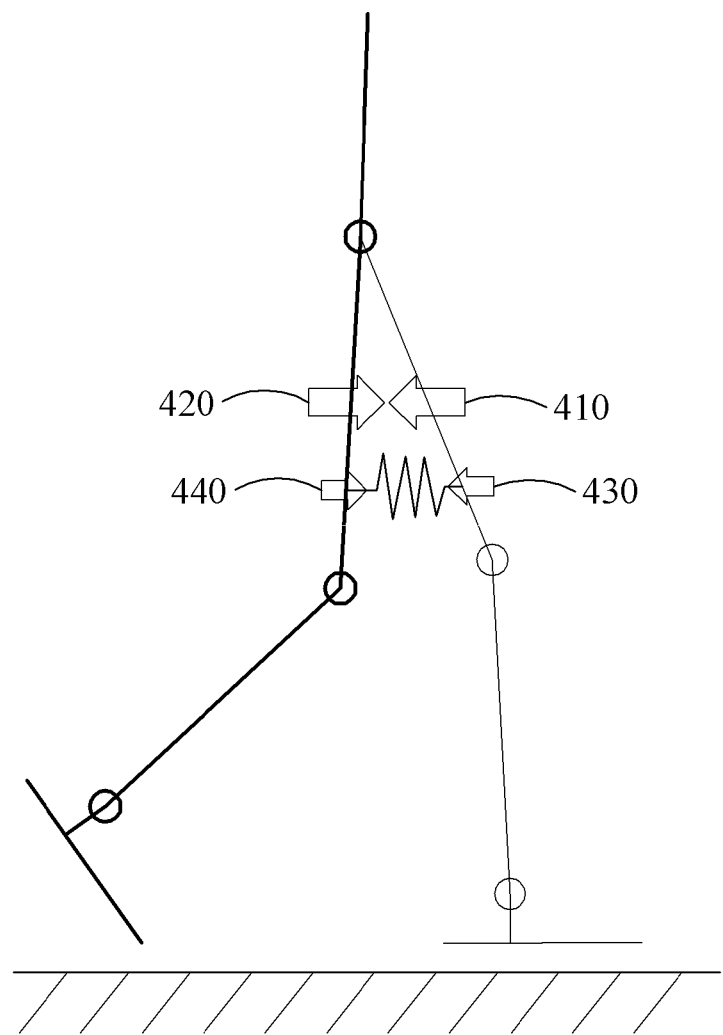
FIG. 4 illustrates an operating principle of a walking assistance apparatus according to at least one example embodiment.

FIGS. 2 through 4 illustrate operating principles of walking assistance apparatuses according to at least one example embodiment. FIGS. 2 through 4 illustrate a portion of gait motions of a user who is wearing a walking assistance apparatus.

Referring to FIG. 2, a gait motion of a user who stands on a right leg and swings a left leg is illustrated. Active assistance forces 210 and 220 to be provided to both legs of a user, respectively, using a motor device may be provided to be suitable for motions of the legs in a gait cycle. In the illustrated example, a direction 230 in which the left leg of the user moves and a direction 240 in which the right leg of the user moves may be the same as directions of a muscular strength and/or an assistance force used for a current gait motion, respectively. In this example, a passive assistance force transmitter may be designed not to apply any force to both the legs of the user.

Referring to FIG. 3, a gait motion of a user in which an angular velocity of a left hip joint is gradually close to "0" as a left leg reduces a forward swinging speed, and similarly an angular velocity of a right hip joint is gradually close to "0" as a right leg reduces a backward swinging speed is illustrated. In the illustrated example, a direction 310 in which the left leg of the user moves and a direction 320 in which the right leg of the user moves may be opposite to directions of a muscular strength and/or an assistance force used for a current gait motion, respectively. In this example, a passive assistance force transmitter may apply passive assistance forces 330 and 340 to the legs of the user using an elastic force in directions in which the legs of the user get close to each other.

Referring to FIG. 4, a gait motion of a user in which a left leg stops swinging and switches to stand, and a right leg stops standing and switches to swing is illustrated. In the illustrated example, a direction 410 in which the left leg of the user moves and a direction 420 in which the right leg of the user moves may be the same as directions of a muscular strength and/or an assistance force used for a current gait motion, respectively. In this example, a passive assistance force transmitter may apply passive assistance forces 430 and 440 to the legs of the user using accumulated elastic energy in directions in which the legs of the user get close to each other.

Figure 5:
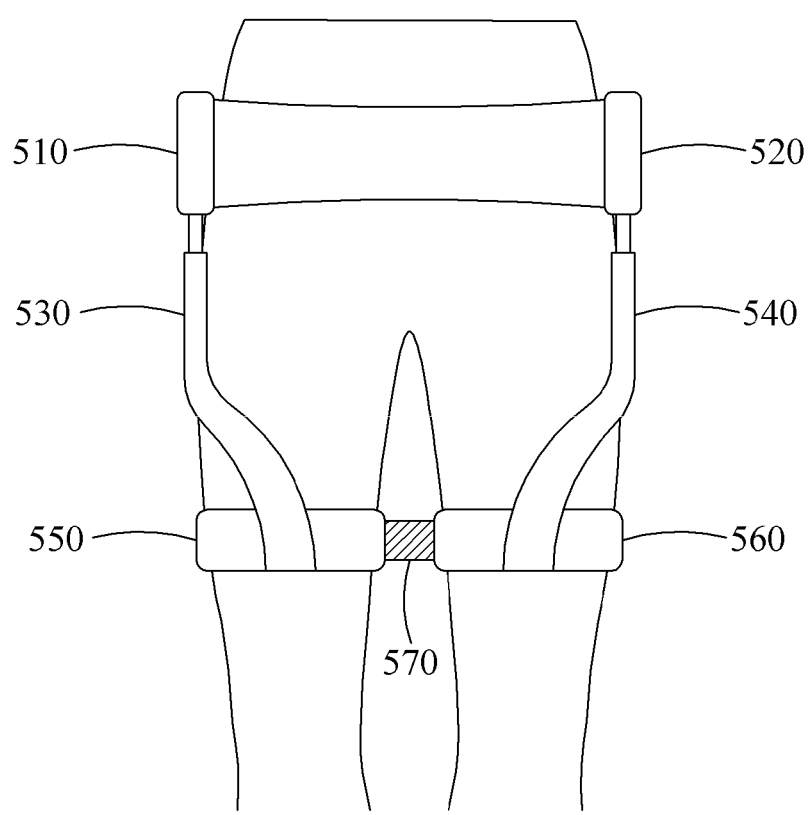
FIG. 5 illustrates an example of a walking assistance apparatus according to at least one example embodiment.
Figure 6:
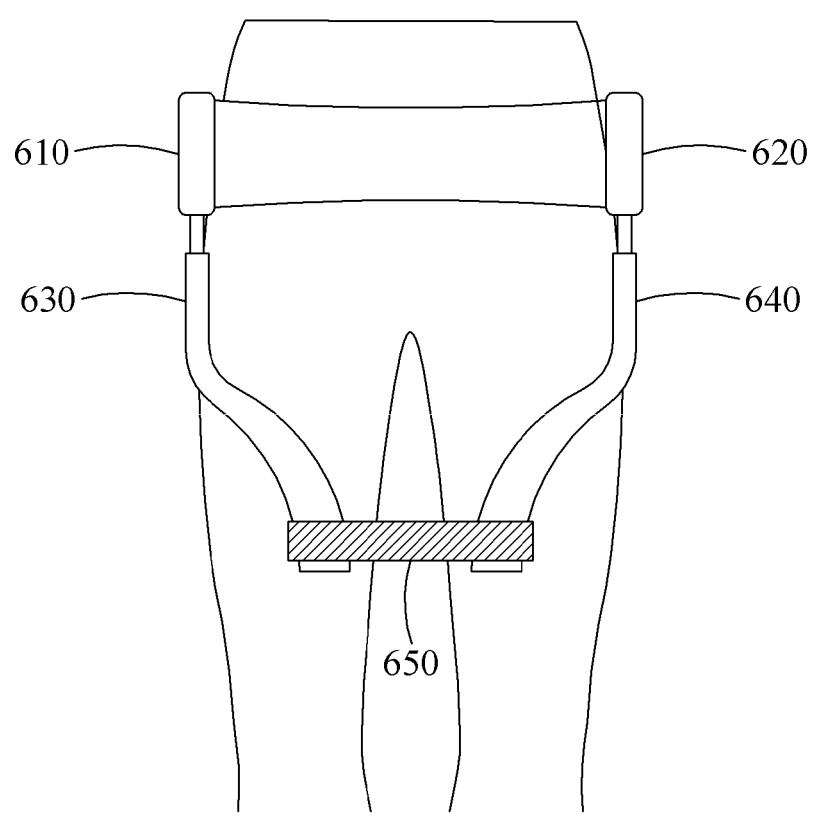
FIG. 6 illustrates an example of a walking assistance apparatus according to at least one example embodiment.
Figure 7:
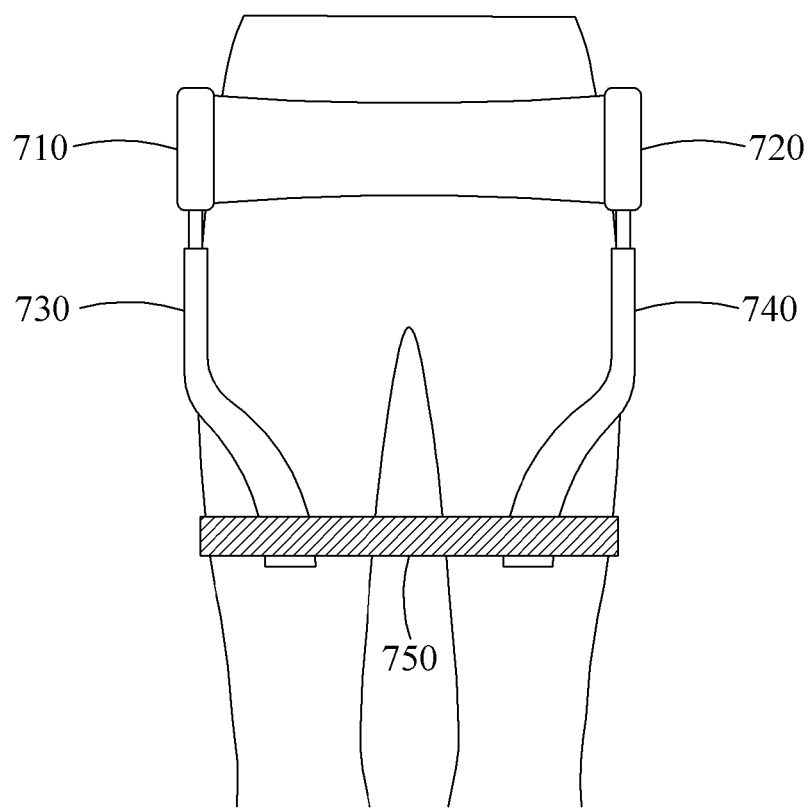
FIG. 7 illustrates an example of a walking assistance apparatus according to at least one example embodiment.

FIGS. 5 through 7 illustrate examples of walking assistance apparatuses according to some example embodiments. A walking assistance apparatus that provides an assistance force to a user only using a motor may be inefficient in terms of energy in a negative work period of a gait cycle. However, in the examples of FIGS. 5 through 7, a walking assistance apparatus may additionally include a passive assistance force transmitter to provide a passive assistance force, thereby improving energy efficiency.

Referring to FIG. 5, a walking assistance apparatus may include a first motor device 510 and a second motor device 520 disposed on both hip joint portions of a user. The walking assistance apparatus may further include a first assistance force transmitter 530 and a second assistance force transmitter 540 configured to transmit an assistance force (or assistance forces) provided by the first motor device 510 and the second motor device 520 to legs of the user, and a first tightener 550 and a second tightener 560 configured to attach the walking assistance apparatus stably to the legs of the user.

The walking assistance apparatus may further include a passive assistance force transmitter 570 configured to connect the first tightener 550 and the second tightener 560. The passive assistance force transmitter 570 may include a desired (or, alternatively predetermined) elastic element (e.g., a rubber band and/or a spring). The passive assistance force transmitter 570 may provide a variable passive assistance force in a direction to pull both the legs of the user toward each other in response to movements of the first tightener 550 and the second tightener 560.

Referring to FIG. 6, a walking assistance apparatus may include a first motor device 610 and a second motor device 620 disposed on both hip joint portions of a user. The walking assistance apparatus may further include a first support 630 and a second support 640 configured to transmit an assistance force provided by the first motor device 610 and the second motor device 620 to legs of the user. Such support may be configured to support a portion of a circumference of a leg of the user, instead of a tightener to be in close contact with the circumference of the leg of the user, thereby mitigating or preventing an inconvenience that the user may experience when wearing the walking assistance apparatus.

The walking assistance apparatus may further include a passive assistance force transmitter 650 configured to connect the first support 630 and the second support 640. The passive assistance force transmitter 650 may include a desired (or, alternatively predetermined) elastic element such as a rubber band and/or a spring. The passive assistance force transmitter 650 may provide a variable passive assistance force in a direction to pull both the legs of the user toward each other in response to movements of the first support 630 and the second support 640.

Referring to FIG. 7, a walking assistance apparatus may include a first motor device 710 and a second motor device 720 disposed on both hip joint portions of a user. The walking assistance apparatus may further include a first support 730 and a second support 740 configured to transmit an assistance force provided by the first motor device 710 and the second motor device 720 to legs of the user.

The walking assistance apparatus may further include a passive assistance force transmitter 750 configured to connect the first support 730 and the second support 740 and enclose both the legs of the user. The passive assistance force transmitter 750 may include a desired (or, alternatively predetermined) elastic element such as a rubber band and/or a spring. The passive assistance force transmitter 750 may provide a variable passive assistance force in a direction to pull both the legs of the user toward each other in response to movements of the first support 730 and the second support 740.

Figure 8:
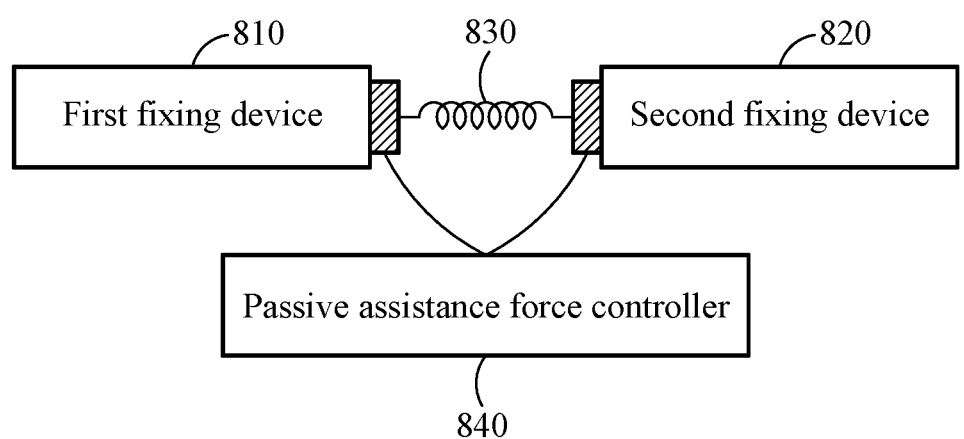
FIG. 8 is a block diagram illustrating a configuration of a walking assistance apparatus according to at least one example embodiment.

FIG. 8 is a block diagram illustrating a configuration of a walking assistance apparatus according to at least one example embodiment. Referring to FIG. 8, a walking assistance apparatus may include a first fixing device 810, a second fixing device 820, a passive assistance force transmitter 830, and a passive assistance force controller 840.

The passive assistance force transmitter 830 is the same as or substantially similar to the passive assistance force transmitter 150 of FIG. 1 in that the passive assistance force transmitter 830 connects the first fixing device 810 and the second fixing device 820 that are attached to both legs of a user, respectively. However, the walking assistance apparatus of FIG. 8 may further include the passive assistance force controller 840 configured to control a property such as a length or an elasticity of the passive assistance force transmitter 830.

The passive assistance force controller 840 may control the length of the passive assistance force transmitter 830 using at least one motor, thereby adjusting a period and a strength at which the passive assistance force transmitter 830 is to be pulled or loosened. That is, by adjusting a magnitude of a passive assistance force to be provided by the passive assistance force transmitter 830 to a desired value through an intervention of the passive assistance force controller 840, an assistance force suitable for a gait motion in a gait cycle may be provided.

The walking assistance apparatus of FIG. 8 may be utilized independently. However, the walking assistance apparatus of FIG. 8 may also be combined with the walking assistance apparatus of FIG. 1 to additionally control a magnitude of a passive assistance force.

Figure 9:
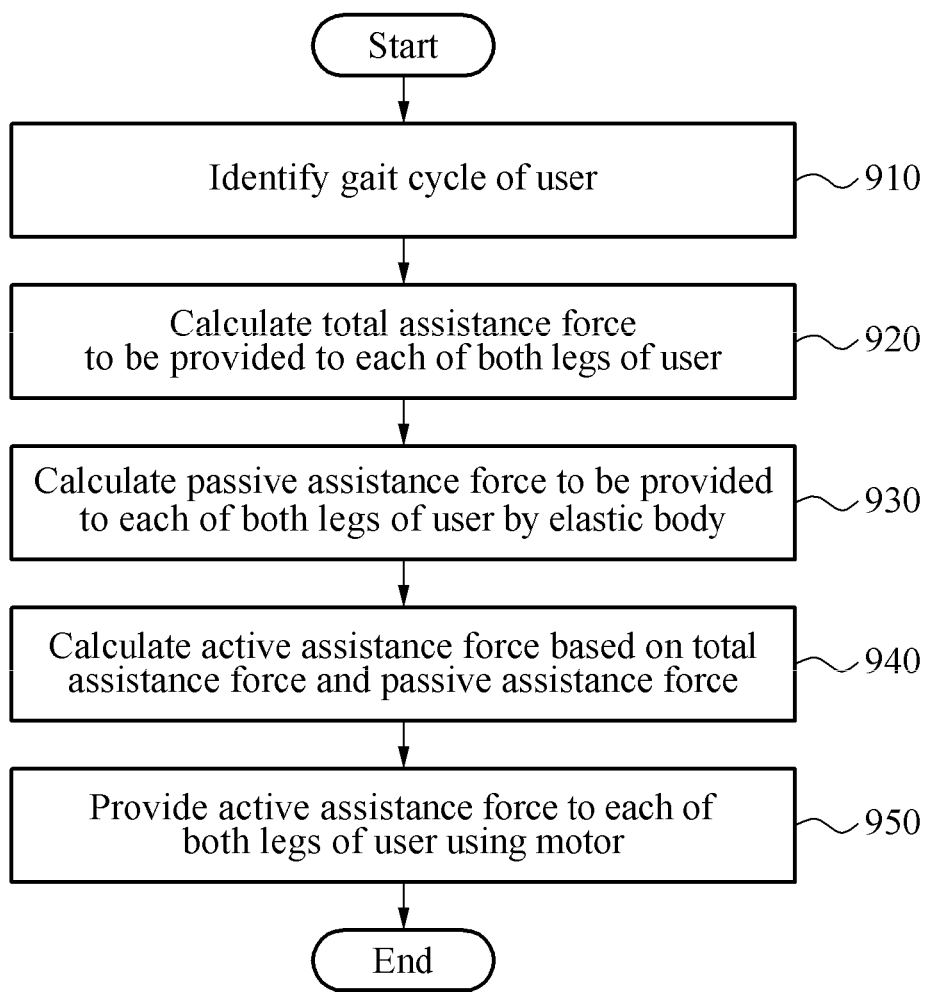
FIG. 9 is a flowchart illustrating an operating method of a walking assistance apparatus according to at least one example embodiment.

FIG. 9 is a flowchart illustrating an operating method of a walking assistance apparatus according to at least one example embodiment.

Referring to FIG. 9, in operation 910, the walking assistance apparatus may identify a gait cycle of a user. The walking assistance apparatus may identify the gait cycle of the user by sensing a parameter associated with a gait motion. The parameter associated with the gait motion may include, for example, angles and angular velocities of both hip joints of the user. The walking assistance apparatus may determine a point of a current gait motion in the gait cycle of the user based on the parameter associated with the gait motion.

In operation 920, the walking assistance apparatus may calculate a total assistance force to be provided to each of both legs of the user. The total assistance force to be provided to each of the legs of the user may vary based on the point of the current gait motion in the gait cycle of the user.

In operation 930, the walking assistance apparatus may calculate a passive assistance force to be provided by a passive assistance force transmitter to each of both the legs of the user. The passive assistance force transmitter may be connected to a first fixing device and a second fixing device attached to both the legs of the user, respectively, to provide a variable passive assistance force in a direction to pull both the legs of the user toward each other in response to movements of the first fixing device and the second fixing device. To improve energy efficiency using the passive assistance force, the walking assistance apparatus may calculate a current magnitude of the variable passive assistance force.

In operation 940, the walking assistance apparatus may calculate an active assistance force to be provided using a motor based on the total assistance force and the passive assistance force. The walking assistance apparatus may calculate a magnitude of the active assistance force by subtracting a contribution portion corresponding to the passive assistance force from the total assistance force. In a case in which the total assistance force and the active assistance force are torques to be applied to a hip joint, and the passive assistance force is an elastic force applied between both fixing devices, the contribution portion corresponding to the passive assistance force may be a value obtained by converting the elastic force to a torque to be applied to the hip joint.

In operation 950, the walking assistance apparatus may provide the active assistance force to each of both the legs of the user using the motor. The active assistance force provided using the motor is a value calculated in operation 940 based on the contribution portion corresponding to the passive assistance force, and thus energy consumption for using the motor may be reduced in a period in which the passive assistance force is applied.

In the scheme as described above, energy consumption for operating a motor in a negative work period during walking may be reduced using a passive assistance force transmitter that connects both legs, and an energy stored in the passive assistance force transmitter may be utilized in a positive work period, whereby energy consumption for operating the motor may be reduced or an additional driving force may be obtained.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable recording medium or media storing program instructions (e.g., computer-readable instructions), which when executed by a computer, configure the computer to perform various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media may include magnetic media (e.g., hard disks, floppy disks, and magnetic tape), optical media (e.g., CD-ROM discs, DVDs, and/or Blue-ray discs), magneto-optical media (e.g., optical discs), and hardware devices that are specially configured to store and perform program instructions (e.g., read-only memory (ROM), random access memory (RAM), flash memory (e.g., USB flash drives, memory cards, memory sticks, etc.)). Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A walking assistance apparatus, comprising:
   a first fixing device and a second fixing device to be attached to both legs of a user, respectively;
   a motor device configured to provide an active assistance force to the first fixing device and the second fixing device using at least one motor; and
   a passive assistance force transmitter connected to the first fixing device and the second fixing device to provide a passive assistance force to the first fixing device and the second fixing device; and a motor device controller configured to control the motor device, wherein the motor device controller is configured to determine a total assistance force to be provided to each of the first fixing device and the second fixing device, and determine a magnitude of the active assistance force based on the total assistance force and the passive assistance force.

2. The walking assistance apparatus of claim 1, wherein the passive assistance force transmitter comprises at least one elastic element, and the passive assistance force transmitter is configured to store an elastic energy while the user is in a negative work period in a gait cycle, and provide the passive assistance force using the elastic energy.

3. The walking assistance apparatus of claim 1, further comprising:

a passive assistance force controller configured to control a magnitude of the passive assistance force provided by the passive assistance force transmitter.

4. The walking assistance apparatus of claim 3, wherein the passive assistance force controller is configured to control the magnitude of the passive assistance force by controlling a length of the passive assistance force transmitter.

5. The walking assistance apparatus of claim 3, wherein the passive assistance force controller is configured to control the magnitude of the passive assistance force using at least one motor connected to at least one end portion of the passive assistance force transmitter.

6. The walking assistance apparatus of claim 1, wherein the motor device controller is configured to control the motor device to adjust the magnitude of the active assistance force provided to the first fixing device and the second fixing device.

7. The walking assistance apparatus of claim 1, wherein the motor device controller is configured to determine the magnitude of the active assistance force based on a magnitude of the passive assistance force.

8. The walking assistance apparatus of claim 1, wherein the motor device controller is configured to calculate the magnitude of the active assistance force by subtracting a contribution portion corresponding to the passive assistance force from the total assistance force.

9. The walking assistance apparatus of claim 1, wherein the first fixing device is attached to a right thigh of the user, and the second fixing device is attached to a left thigh of the user.

* * * * *